(12) United States Patent
Flach et al.

(10) Patent No.: US 7,551,968 B2
(45) Date of Patent: Jun. 23, 2009

(54) STIMULATION ELECTRODE LEAD

(75) Inventors: Erhard Flach, Berlin (DE); Thomas Töllner, Berlin (DE); Ole Grauhan, Berlin (DE)

(73) Assignee: Biotronik CRM Patent AG (CH)

( * ) Notice: Subject to any disclaimer, the term of this patent is extended or adjusted under 35 U.S.C. 154(b) by 615 days.

(21) Appl. No.: 11/186,410

(22) Filed: Jul. 21, 2005

(65) Prior Publication Data
US 2006/0074472 A1    Apr. 6, 2006

(30) Foreign Application Priority Data
Jul. 23, 2004   (DE) ................. 10 2004 036 397

(51) Int. Cl.
*A61N 1/05* (2006.01)
(52) U.S. Cl. ...................................... 607/122
(58) Field of Classification Search .......... 607/122, 607/127, 115, 116, 119, 123, 125, 131
See application file for complete search history.

(56) References Cited
U.S. PATENT DOCUMENTS

| | | | | |
|---|---|---|---|---|
| 5,381,790 A | * | 1/1995 | Kanesaka ................ 600/381 |
| 5,387,233 A | * | 2/1995 | Alferness et al. ............ 607/126 |
| 5,925,073 A | | 7/1999 | Chastain et al. |
| 6,129,749 A | * | 10/2000 | Bartig et al. ................ 607/122 |
| 2003/0195603 A1 | * | 10/2003 | Scheiner et al. ............ 607/122 |
| 2003/0220677 A1 | * | 11/2003 | Doan et al. ................ 607/122 |

* cited by examiner

*Primary Examiner*—Mark W Bockelman
*Assistant Examiner*—Roland Dinga
(74) *Attorney, Agent, or Firm*—Hanh Loeser & Parks LLP (57) ABSTRACT

A stimulation electrode lead for connecting to an electrotherapy device such as a pacemaker, a defibrillator or the like, is disclosed. The stimulation electrode lead is configured for intraluminal placement within a blood vessel or within the heart of a patient, and comprising a proximal and a distal end, an electrode lead plug at the proximal end of the stimulation electrode lead, and the stimulation electrodes in the region of the distal end of the stimulation electrode lead, said stimulation electrodes having an electrically conductive outer surface and being connected electrically to the electrode lead plug, the stimulation electrode lead having at least one distal electrode support member in the region of its distal end, said support member supporting at least one electrode and being connected by a conductor link to a distal end of a first, extended portion of the electrode lead, wherein the conductor link is preformed so that when in the relaxed state it is not extended and can be elastically extended.

26 Claims, 8 Drawing Sheets

STIMULATION ELECTRODE LEAD

CROSS-REFERENCE TO RELATED APPLICATIONS/INCORPORATION BY REFERENCE

This U.S. patent application claims priority to and the benefit of German patent application serial number 10 2004 036 397.8 filed on Jul. 23, 2004.

TECHNICAL FIELD OF THE INVENTION

Embodiments of the present invention relate to a stimulation electrode lead for connecting to an electrotherapy device, in particular an implantable electrotherapy device such as a pacemaker, a defibrillator/cardioverter, or the like.

BACKGROUND OF THE INVENTION

When a stimulation electrode lead has been implanted and connected to a electrotherapy device, for example to a pacemaker or defibrillator, the electrical stimulation pulses supplied by the pacemaker or defibrillator are delivered, for example, to one of the chambers of the heart. Said chamber is usually the right ventricle, since stimulation electrode leads are usually inserted via the vena cava superior and the right atrium of the heart into the right ventricle. Many patients can be helped by stimulating just the right ventricle.

Dual-chamber pacemakers are also known that co-operate not only with electrodes in the right ventricle, but for which electrodes are also provided in the right atrium, so that both the right atrium and the right ventricle can be stimulated. In this way it is also possible to help those patients who lack natural synchronization of the right atrium and right ventricle. In a healthy person, the right atrium firstly contracts after being stimulated by the sinus node. After a certain time delay, the right ventricle contracts as a result of atrioventricular conduction. The heart functions optimally when this atrioventricular conduction time is physiologically well adjusted.

It is now known also that not only the right atrium and right ventricle of a heart can be stimulated, but also the left ventricle. This is particularly interesting for patients who suffer from congested heart failure (CHF). One problem associated with the left ventricle stimulation desired in such cases is that it is not easy to implant an electrode lead assigned to the left ventricle. One known option is to insert an electrode lead for the left ventricle through the vena cava superior and the right atrium into the coronary sinus and to place electrodes in the coronary sinus or in a lateral vein branching off it. Due to the fact that the latter blood vessels are very limited in diameter, the constructional requirements for an appropriate electrode lead are especially high. Firstly, it is essential, of course, that the electrode lead does not restrict the flow of blood through these blood vessels to any incompatible extent. Secondly, there is always the problem of ensuring that the electrode lead is suitably fixated in these blood vessels. Secure fixation of the electrode lead is also important, because ideal settings for a pacemaker must always be found for a given stimulation site, and such adjustment cannot be repeated as frequently as desired.

Known solutions for coronary sinus electrodes (comprising electrode leads with stimulation electrodes for placement in the coronary sinus or in a lateral vein branching off it) are dissatisfying in various respects, so there is still a need for a coronary sinus electrode that avoids the respective drawbacks of the known prior art.

SUMMARY OF THE INVENTION

This need is met by the various embodiments of the present invention of the present application with a stimulation electrode lead of the kind specified herein.

The stimulation electrode lead is configured for intraluminal placement within a blood vessel or within the heart of a patient, and has a proximal and a distal end. An electrode lead plug is provided at the proximal end of the electrode lead. At its distal end, the stimulation electrode lead carries stimulation electrodes that have an electrically conductive outer surface and are electrically connected to the electrode lead plug such that the stimulation pulse or defibrillation shock can be delivered at the distal end by the electrotherapy device via the electrode lead plug, the stimulation electrode lead and its electrically conductive outer surface.

At its distal end, the stimulation electrode lead has at least one distal electrode support member that supports at least one electrode and is connected by a conductor link to a distal end of a first, extended portion of the electrode lead.

The first portion of the electrode lead at the proximal end of the conductor link includes a lumen and can be structured like conventional electrode leads, whereas the conductor link does not need to have a lumen, is substantially thinner and may be more flexible than the first portion of the electrode lead, since in a minimal case the conductor link needs only to have an extended and flexible electrical conductor, and an insulating sleeve made of plastic, for example.

The distal electrode support member at the distal end of the conductor link may have a larger diameter than the conductor link with the result that, in the electrode lead according to an embodiment of the present invention, a comparatively thick, a comparatively thin and then a comparatively thicker electrode lead portion succeed each other in the longitudinal direction.

The conductor link is formed in such a way that when in the relaxed state it is not extended and can be elastically extended. In other words, the conductor link is somehow curved or folded when in its relaxed, preformed state, and can be stretched elastically from this state. This elastic stretching is similar to that of a tension spring, but with the difference that the conductor link may be fully extendable without losing its ability to re-adopt its curved, spiral or folded state. The latter feature is desirable with regard to fixating the electrode lead in the respective blood vessel. The electrode lead of certain embodiments of the present invention can be fully extended for insertion into the blood vessel, thus facilitating insertion. Once in place, the electrode lead is allowed to relax and adopt a spiral, curved or folded shape with which the electrode lead plug anchors itself inside the blood vessel.

In a variant embodiment of the present invention, the prior shape given to the electrode lead and which the lead seeks to adopt when in the relaxed state can be predefined by an elastic preformed plastic sleeve around an electrical conductor. Said electrical conductor contacts the electrode on the distal electrode member and connects the latter to the electrode lead plug at the proximal end of the electrode lead.

Certain shapes for the preformed conductor link are a snake shape or a helix.

In addition, the conductor link may have a significantly smaller diameter than the distal electrode support member.

In a variant embodiment of the present invention, the stimulation electrode lead can have a second, proximal electrode support member at the distal end of the first, extended portion of the electrode lead. This second electrode support member may have a larger diameter than the conductor link and the portion of the first, extended portion of the electrode lead which at least adjoins the proximal electrode support member. The proximal electrode support member is thus disposed between the conductor link and the first, extended portion of the electrode lead. The conductor link connects the proximal and the distal electrode support members. The stimulation electrode lead terminates at the distal electrode support member. The electrode support members may have approximately the same outer diameter.

A distal opening may be provided in the proximal electrode support member, through which opening a guide wire or an implantation tool similar to a guide wire can exit the stimulation electrode lead. A longitudinal opening may be provided in the distal electrode support member, through which opening such a guide wire can enter and may pass through. This permits the distal electrode lead member, which is effectively connected only by a relatively thin, flexible conductor link to the rest of the stimulation electrode lead, to be threaded onto a relatively stiffer guide wire.

The longitudinal opening in the distal electrode support member can have a stepped inner diameter that is smaller in the distal direction than in the direction facing the proximal electrode support member. Thus it is possible, for example, for a guide wire or implantation tool to be inserted in its entirety through the distal electrode support member. A sleeve or insertion tube that has an outer diameter too large to fit through the longitudinal opening in the distal electrode support member and which can be used to stretch the conductor link by means of a push imparted by the sleeve or the insertion tube, can then be pushed onto the guide wire. To achieve this, it suffices that the longitudinal opening in the distal electrode support member has a smaller inner diameter than the distal opening in the proximal electrode support member. The smallest diameter of the longitudinal opening in the distal electrode member is sized to permit a guide wire to be fed through, but does not permit a sleeve pushed onto the guide wire to pass through.

A suitable implantation tool comprises at least one tube having a lumen that allows the tube to be pushed over a conventional guide wire. The tube, also referred to hereinafter as the "insertion tube", should be stiff enough to be able to advance the electrode support member. To couple the insertion tube to the distal electrode support member, for example, the longitudinal opening in the distal electrode member can have, at least in part, a diameter that is smaller than the outer diameter of the insertion tube, such that the insertion tube cannot be fed through the longitudinal opening, in its entirety at least, but instead takes the distal electrode member along with it when the insertion tube is advanced. In any case, the longitudinal opening in the distal electrode support member should be sized such that the guide wire itself can be fed in its entirety through the electrode support member.

In this variant embodiment of the present invention, the implantation tool can comprise a second insertion tube of larger diameter, wherein said insertion tube can be pushed over the aforementioned insertion tube and is unable, at least in its entirety, to pass through the longitudinal opening in the proximal electrode support member in order to take along the proximal electrode support member. A more detailed description of this variant embodiment of the present invention can be obtained from the description of FIGS. 1-6.

In an alternative variant embodiment of the present invention, a double-walled insertion tube is provided that supports an expandable balloon at its distal end. Said balloon can be expanded by means of a fluid that is fed through the double wall of the insertion tube into the balloon. The double wall of the insertion tube is defined by an inner and an outer insertion tube that enclose a free space through which the fluid for expanding the balloon can be supplied. Such a double-walled insertion tube with a balloon at the distal end can be coupled to one of the two electrode support members by inserting the balloon at the distal end of the double-walled insertion tube into one of the longitudinal openings of the two electrode support members and then expanding it so that the double-walled insertion tube and the respective electrode support member are coupled to each other by frictional or positive engagement due to the balloon expanding. Although this variant of an implantation tool, an alternative to the previously described variant embodiment of the present invention involving an implantation tool with two separate and independent insertion tubes, is more complex due to the balloon that is required, it allows the electrode support member not only to be advanced by means of the double-walled insertion tube, but also to be withdrawn, if desired. In order to implant the electrode lead, the balloon of the double-walled insertion tube is coupled to the distal electrode support member to enable the distal electrode support member to be advanced along a previously inserted guide wire. When this happens, the conductor link between the two electrode support members is stretched, with the result that the conductor link cannot become entangled with the vascular walls.

The two electrode support members may be plastic or ceramic members, so that they are both biocompatible and electrically insulating. Each electrode support member may be between 1 and 3 mm long.

The purpose of the aforementioned measures is to enable a distal end portion of the first, extended portion of the electrode lead, the electrode member(s) and the conductor link to be placed within the coronary sinus or in a lateral vein branching off the coronary sinus. In a certain variant embodiment of the present invention, this purpose defines the dimensions of the components of the stimulation electrode leads for which protection is claimed.

An embodiment of the present invention also includes an overall system that also comprises an implantation tool of the kind described above, in addition to the electrode lead described above.

BRIEF DESCRIPTION OF THE DRAWINGS

An embodiment of the present invention shall now be explained in greater detail with reference to the Figures. The Figures show in FIG. 1 an overview of the distal end of a stimulation electrode lead according to an embodiment of the present invention.

DETAILED DESCRIPTION OF THE INVENTION

Figure 1:
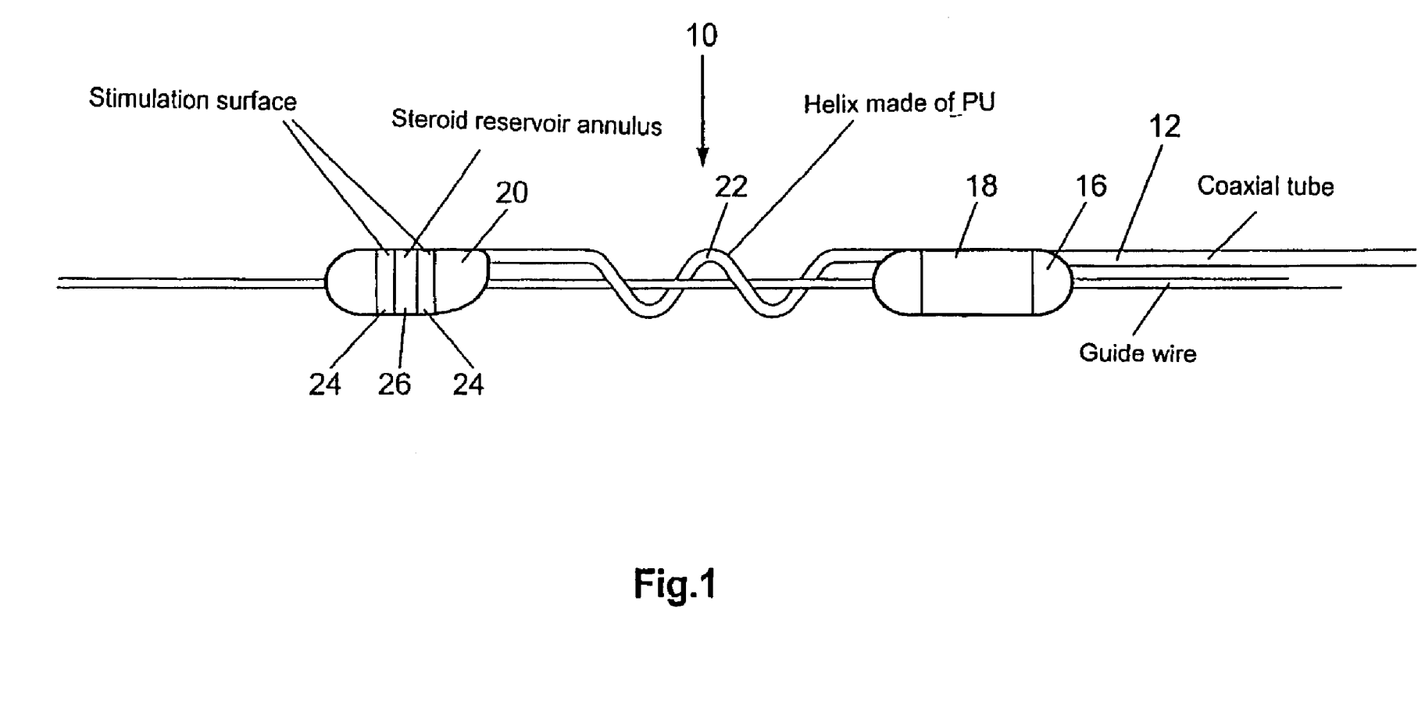

FIG. 1 gives an overview of the distal end of a stimulation electrode lead 10 according to an embodiment of the present invention. A proximal lead portion 12 extending beyond the right-hand edge of the drawing and FIG. 1 to an electrode lead plug 14 at a proximal end of the electrode lead can be seen; see also FIG. 3. Inside proximal electrode lead portion 12, at least two electrical conductors are disposed with which electrodes at the distal end of electrode lead 10 are electrically connected to corresponding contact surfaces of electrode lead plug 14. The proximal electrode lead portion 12 can be structured in a known manner, meaning that it comprises, for example, a helical wire spiral shielded by an insulating and sealing plastic sleeve. It may comprise two electrically conductive wires encased in an insulating sleeve made of polyurethane.

At the distal end of the proximal electrode lead portion 12, a first electrode support member 16 with a stimulation electrode 18 of large area is disposed, said electrode having an electrically conductive outer surface.

Distally removed from the first electrode support member 16 there is a second, distal electrode support member 20 connected via a helically preformed conductor link 22 of small outer diameter to the first electrode member 16.

The second, distal electrode support member 20 has a second stimulation electrode with two electrically conductive stimulation electrodes 24, between which a steroid reservoir 26 of annular shape is disposed. The second stimulation electrode with stimulation surfaces 24 is connected by an electrical conductor inside conductor link 22 and by the proximal electrode lead portion to a contact surface on electrode lead plug 14.

Each of the electrode members, namely the first, proximal electrode member 16 and the second, distal electrode member 20, have a central longitudinal bore, the diameter of the central longitudinal bore in the second, distal electrode member 20 being smaller, at least across part of the length of the longitudinal bore, than the longitudinal bore in the first, proximal electrode support member. The longitudinal bores in the two electrode support members 16 and 20 serve to receive a guide wire 30, which is likewise shown in FIG. 1. Wire guide 30 is also shown separately in FIG. 2.

Figure 2:
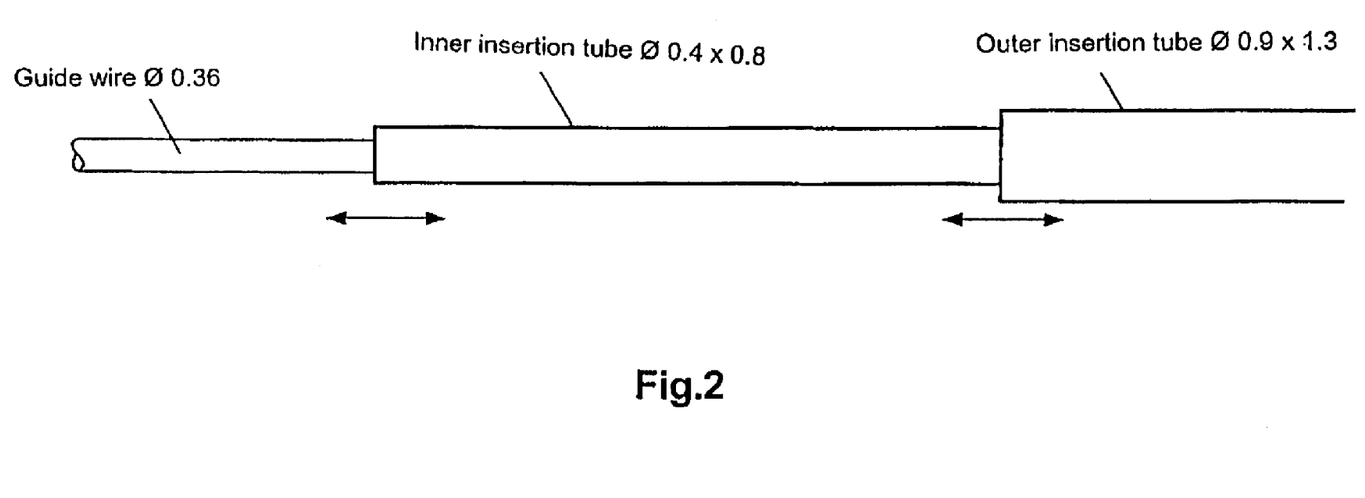
FIG. 2 a schematic view of a guide wire encased by an inner and outer insertion tube as insertion sleeves for implanting the stimulation electrode leads shown in FIG. 1.

It can be seen from FIG. 2 that guide wire 30 has a three-part structure, comprising a guide wire in the narrower sense (32) and with a diameter of 0.36 mm, over which an inner insertion tube with an inner diameter (inner lumen) of 0.4 mm and an outer diameter of 0.8 mm is pushed. An outer insertion tube 36 is pushed over said inner insertion tube 34, said outer insertion tube having a lumen of inner diameter 0.9 mm, and having an outer diameter of 1.3 mm. The guide wire in the narrower sense (32) is structured and can be steered in the same way as known guide wires. The inner insertion tube 34 is sized such that it can be fed in its entirety through the longitudinal bore in the first, proximal electrode support member 16, but not through the longitudinal bore in the second, distal electrode member 20. Only the guide wire in the narrower sense (32) can be fed in its entirety through the longitudinal bore of the second, distal electrode member 20. The longitudinal bore in the first, proximal electrode member 18 is sized such that the inner insertion tube 34 can be fed in its entirety through said longitudinal bore, whereas the outer insertion tube 36 cannot.

This permits the guide wire in the narrower sense (32) to be threaded firstly through both electrode support members 16 and 20 such that the guide wire in the narrower sense (32) forms a guide member for both electrode support members. In order to advance both electrode support members 16 and 20 along the guide wire in the narrower sense (32), the inner insertion tube 34 and the outer insertion tube 36 are advanced synchronously. The second, distal electrode member 20 is moved in the process by inner insertion tube 34, because said inner insertion tube 34 cannot be fed in its entirety through the longitudinal bore in the second, distal electrode member 20. The first, proximal electrode lead member 16 is advanced by the outer insertion tube 36.

Figure 3:
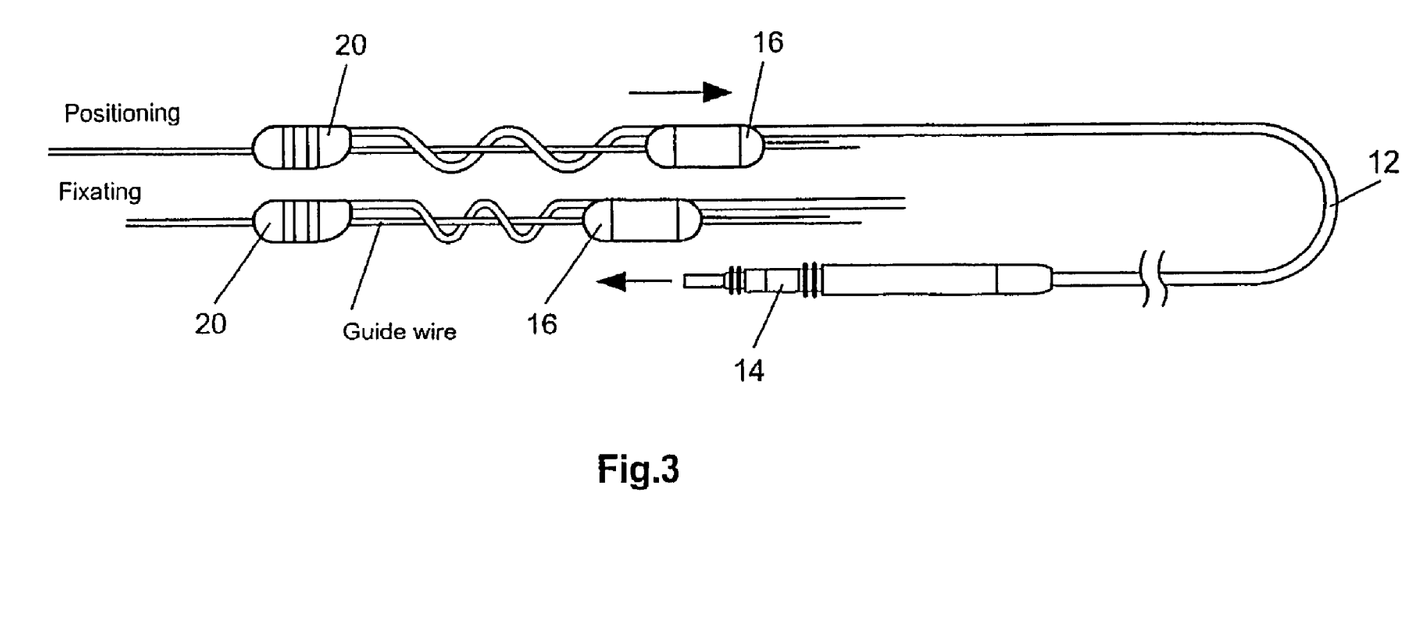
FIG. 3 a sketch of the electrode lead in two different states, namely one state in which the conductor link is extended, and one state in which the conductor link is relaxed.

When advancing the two insertion tubes 34 and 36 to insert electrode lead 10, the two insertion tubes are positioned in relation to each other such that conductor link 22 is substantially extended. This is shown in FIG. 3a. Once the second, distal electrode support member 20, in particular, has been correctly in this manner, only the outer insertion tube 36 is advanced, and no longer the inner insertion tube 34. This results in the first, proximal electrode member 16 being advanced to a position closer to the second, distal electrode member 20, such that conductor link 22 is no longer in the substantially extended state as shown in FIG. 3a, but instead adopts its original, preformed, helical spiral shape. This helical spiral shape of conductor link 22 (see FIG. 3b) results in the two electrode support members 16 and 20 being fixed in position by the conductor link, which is now in contact with a vascular wall.

Attention is drawn to the fact that, in the embodiment shown in FIGS. 1-3, both of the electrode support members 16 and 20 have a diameter that is more than double the diameter of the proximal electrode lead portion 12. The through bore in the first, proximal electrode member 16 has two openings at the proximal and at the distal end, respectively, of the first, proximal electrode member 16. This enables guide wire 30 to be inserted into the longitudinal bore in the first electrode support member 16 adjacent the location where the proximal electrode lead portion 12 attaches to the first electrode member 16. It is also possible, as an alternative, to provide a guide wire lumen in the proximal electrode lead portion 12, said guide wire lumen opening directly into the first electrode support member such that guide wire 30 can be fed through the inside of proximal electrode lead portion 12. Although this variant embodiment of the present invention may also have advantage, the variant embodiment of the present invention as shown in FIGS. 1-3 may be preferred, because guide wire 30 with its two encasing insertion tubes 34 and 36 has a larger diameter than a standard guide wire in the narrower sense. Furthermore, the variant embodiment of the present invention shown in FIGS. 1-3 prevents the type of problems that can result from a patient's blood entering a guide wire lumen in the proximal portion of the electrode lead.

Figure 4:
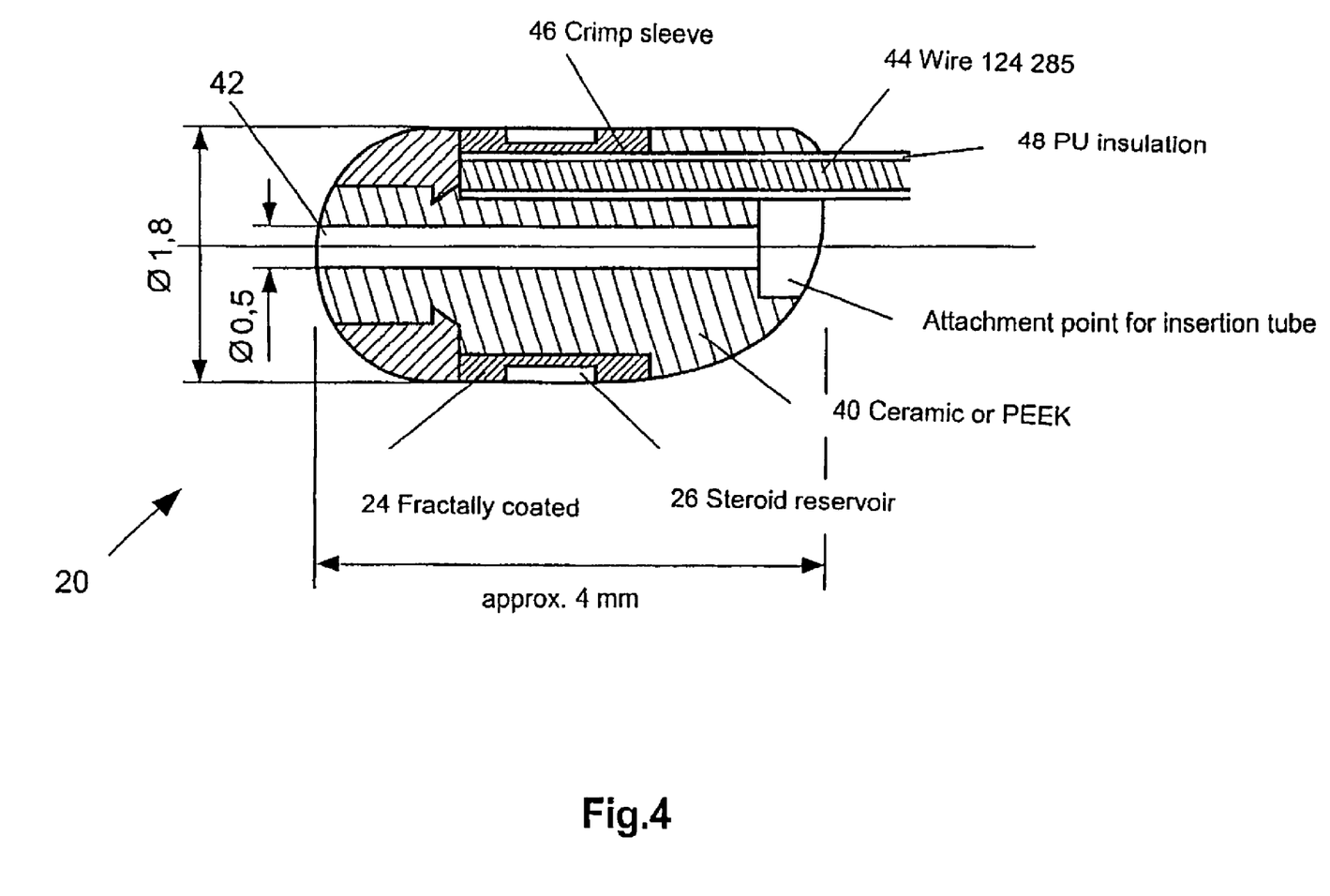
FIG. 4 a longitudinal section through the distal electrode lead member.

FIG. 4 shows a longitudinal section through the distal electrode support member of the variant embodiment of the present invention in FIGS. 1-3. As can be seen from FIG. 4, the distal electrode support member 20 has a base member made of ceramics or PEEK (polyether ether ketone). Base member 40 is provided with a stepped longitudinal bore 42 of inner diameter 0.5 mm in the distal portion of base member 40 and a larger diameter at the proximal end as a point of attachment for inner insertion tube 34. Base member 40 carries an annular electrode as distal electrode, with fractally coated electrode surfaces 24. A ring groove for receiving the steroid reservoir 26 is provided in the distal electrode. The distal electrode is in electrical contact with an electrically conductive wire 44 and a crimp sleeve 46 crimped onto the distal end of wire 44. At its proximal end, wire 44 runs inside an insulating polyurethane sheath 48 and in conjunction with the latter forms conductor link 22.

The distal electrode support member 20 is approximately 4 mm in length and has an outer diameter of about 1.8 mm.

Figure 5A:
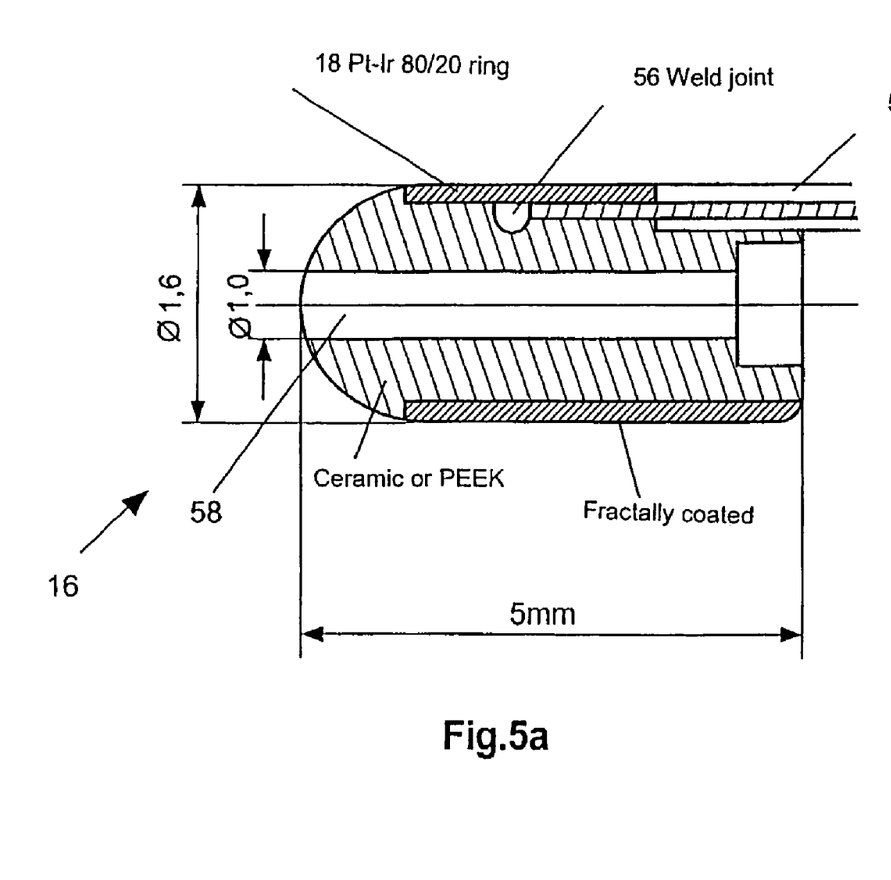
FIGS. 5*a* and *b* cross-sectional views of the proximal electrode support members.
Figure 5B:
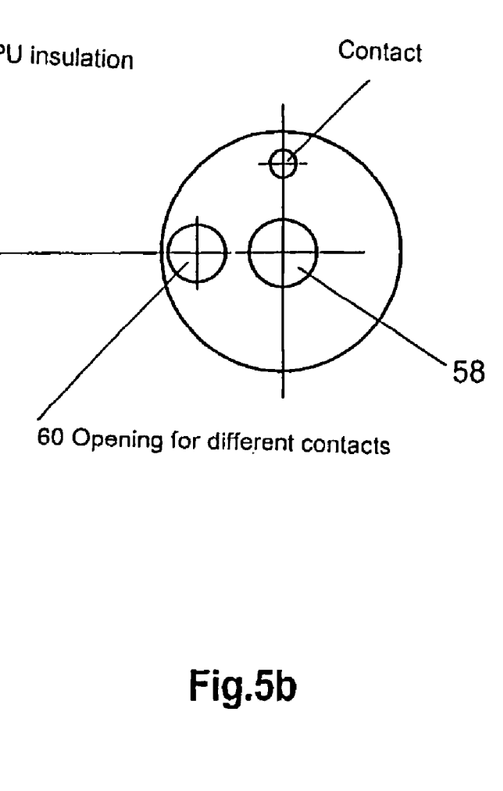

FIG. 5 shows the first, proximal electrode support member 16 in longitudinal and transverse cross-section. Electrode support member 16 likewise has a base member 50 made of ceramics or PEEK. Base member 50 supports an annular electrode 18 of large area, which after implantation acts as an indifferent electrode due to its surface area.

The proximal electrode lead portion 12 is connected directly to the proximal electrode support member 16. Said proximal electrode lead portion 12 likewise has an insulating polyurethane sheath 52 enclosing the two electrically conductive wires, of which a second electrically conductive wire 54 is shown in FIG. 5. The second electrically conductive wire 54 is connected to electrode 18 by a weld joint 56.

Electrode 18 is made of an 80/20 platinum-iridium alloy.

A longitudinal bore 58 is provided in base member 50, said bore having an inner diameter of 1.9 mm in its distal portion and in its proximal portion a guide element of larger diameter for receiving the distal end of outer insertion tube 36. FIG. 5b shows a cross-section through the proximal electrode support member 16, with a through bore 60 for connecting conductor link 22 and hence for contacting the distal surfaces of electrode 24. The proximal electrode support member 16 is approximately 5 mm in length and has an outer diameter of about 1.6 mm.

Figure 6:
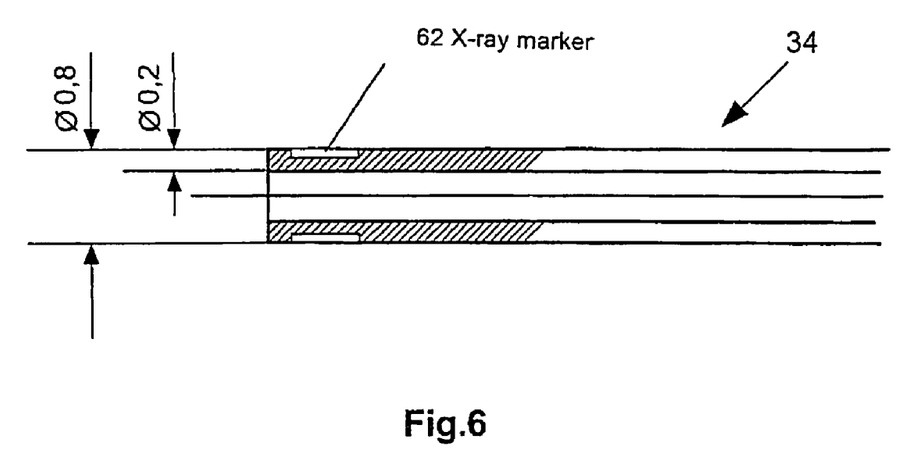
FIG. 6 a detail of a distal end of a suitable insertion tube.

FIG. 6 shows the distal end of inner insertion tube 34. It can be seen that inner insertion tube 34 has an X-ray marker 62 at its distal end, in the form of a ring of X-ray radio-opaque material, for example gold. X-ray marker 62 is used for exact positioning of inner insertion tube 34 and hence of distal electrode 20.

Figure 7:
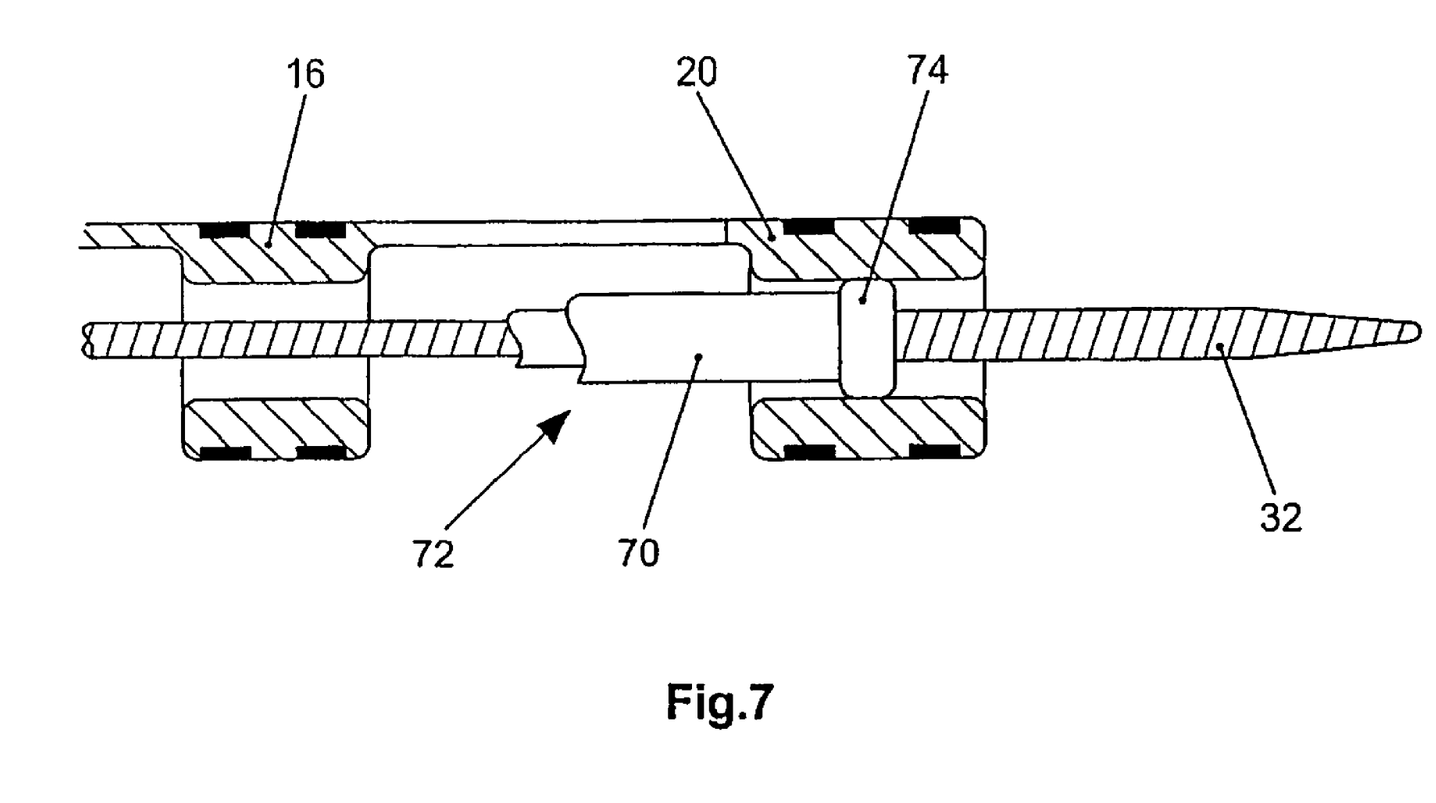
FIG. 7 an alternative variant of a distal end of an electrode lead, with an alternative implantation tool.

FIG. 7 shows the distal end of a stimulation electrode lead similar to that in FIGS. 1-6, with an alternative implantation tool 70 comprising a double-walled insertion tube 72 with an expandable balloon 74 at its distal end. The double-walled insertion tube 72 takes the form of an inner insertion tube 72a and an outer insertion tube 72b. Between the two tubes there is a free space through which a fluid is fed into balloon 74 in order to expand it. Inner insertion tube 72a also has a lumen to enable the double-walled insertion tube 72 to be pushed over a guide wire 32.

Electrode support members 16/ and 20/ in FIG. 7 differ from electrode support members 16 and 20 in FIGS. 1-5 in that the respective longitudinal bores in the two electrode support members 16/ and 20/ have identical end-to-end diameters.

Figure 8:
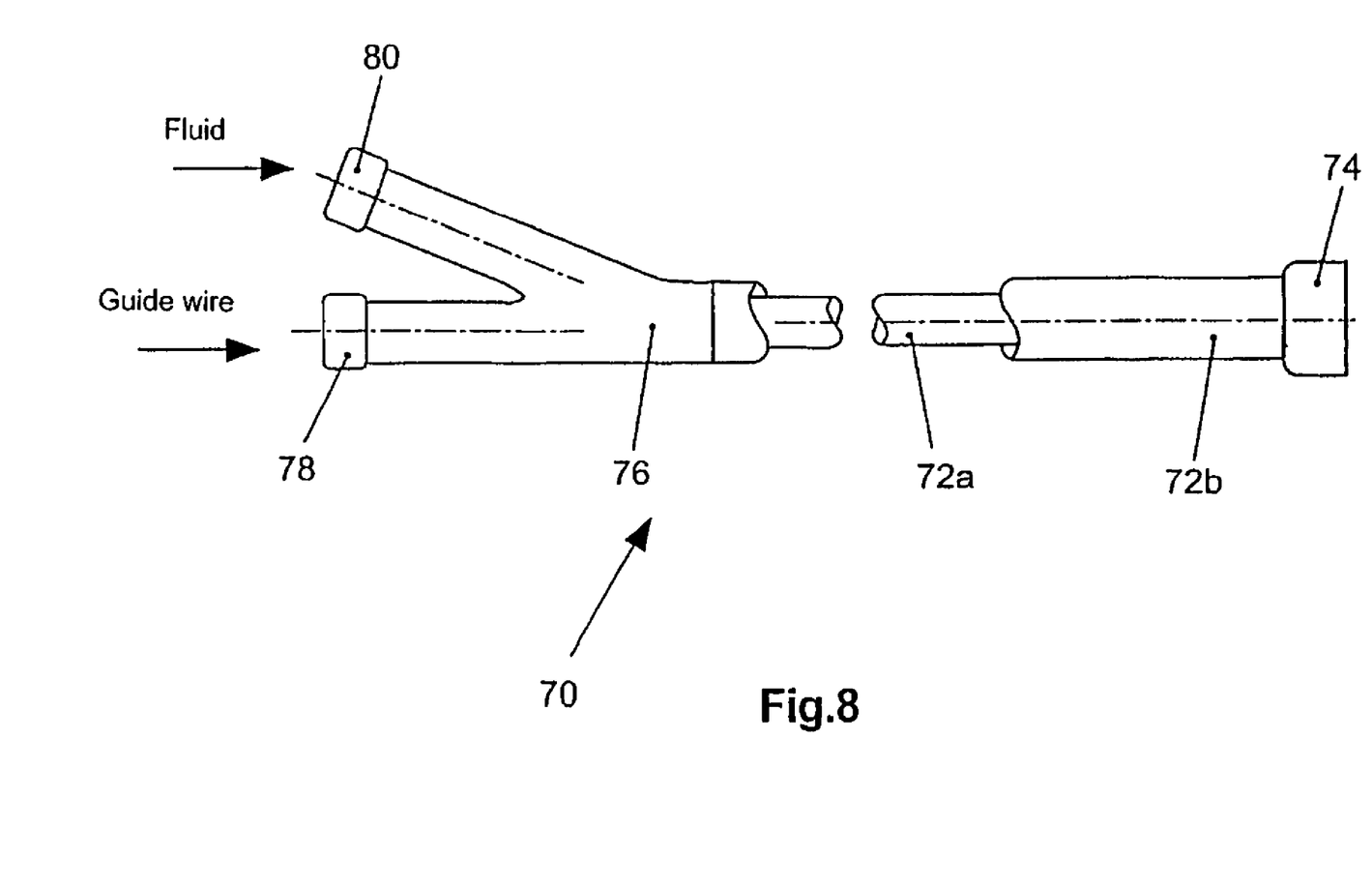
FIG. 8 a schematic view of a proximal end and the distal end of the implantation tool in FIG. 7.

FIG. 8 shows a possible structure for a proximal end of implantation tool 70. The double-walled insertion tube 70 opens into a Luer Y-fitting 76 having a first port 78 connected to the guide wire lumen enclosed by inner insertion tube 72a, and by means of which port a guide wire can be advanced. A second port 80 is connected to the cavity enclosed between inner insertion tube 72a and outer insertion tube 72b, and serves the purpose of feeding fluid into balloon 74 in order to expand balloon 74.

Balloon 74 consists of an elastic material enabling it to expand when a fluid is fed into balloon 74 under pressure, and to return to its original, smaller outer diameter as soon as the fluid pressure decreases. A medium suitable as fluid is a biocompatible infusion solution, for example, leakages of which are unproblematic. A pump for changing the fluid pressure in balloon 74 can be connected to the second port 80 of the Luer fitting 76.

The implantation tool 70 can have visual length markings in its proximal portion, or additionally or alternatively can have X-ray markers in its distal portion in order to indicate the relative axial position of the stimulation electrode lead and the implantation tool. This enables balloon 74 of the implantation tool to be placed within the desired electrically active electrode surfaces of the stimulation electrode lead.

The shaft of implantation tool 70 formed by double-walled tube 72 is fabricated with a sufficiently stable tubing material in order to transfer a steering movement initiated at the proximal end of Luer Y-fitting 74 with little loss as far as the distal end and onto an electrode support member coupled via balloon 74 to implantation tool 70.

To implant a stimulation electrode lead 10 with the aid of implantation tool 70, a venous puncture is made at a suitable location. A guide wire is then laid, which means its distal end is advanced until the distal end has passed the location where electrode support members 16 and 20 or stimulation electrode lead 10 are to be positioned. The implantation tool 70 is then pushed onto the guide wire using the lumen inside the inner insertion tube 72a. The implantation tool 70 and the stimulation electrode lead 10 may be coupled to each other in the region of the distal electrode support member 20 via inflated balloon 74. The implantation tool 70, including the coupled stimulation electrode lead 10, can then be advanced along the guide wire.

If the stimulation electrode lead 10 is already positioned in a blood vessel and the implantation site for the electrode support member is to be modified, the guide wire 32 is first fed through the longitudinal openings in the two electrode support members. The implantation tool, with deflated balloon, is then advanced until the deflated balloon has reached a desired position inside the longitudinal opening in the distal electrode support member, for example. Balloon 74 is then pumped up in order to couple the distal electrode support member with the implantation tool. It is then possible to alter the position of the distal electrode support member.

The position of the proximal electrode support member relative to the position of the distal electrode support member, and hence the extent to which the conductor link is stretched can be adjusted by inserting the deflated balloon into the longitudinal opening in the proximal electrode member and expanding it there. The proximal electrode support member can then be positioned accordingly. When both electrode support members have taken up position at the desired implantation site, implantation tool 70 can be removed once the balloon has been deflated.

The surfaces of the longitudinal openings in the electrode support members, and the surface of the balloon are designed so that, on the one hand, it is possible to couple the balloon securely to the respective electrode support member when the balloon is expanded. On the other hand, it should be possible to insert the deflated balloon with as little friction as possible through the longitudinal openings in the electrode support members and through the respective lumen of the stimulation electrode lead. Frictions between the lumen enclosed by inner insertion tube 72a and guide wire 32 should likewise be kept as low as possible.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A stimulation electrode lead for connecting to an electrotherapy device such as a pacemaker or a defibrillator, the stimulation electrode lead being configured for intraluminal placement within a blood vessel or within a heart of a patient, said stimulation electrode lead comprising:

a proximal end;
a distal end;
an electrode lead plug at the proximal end of the stimulation electrode lead;
stimulation electrodes at the distal end of the stimulation electrode lead, the stimulation electrodes having an electrically conductive outer surface and being electrically connected to the electrode lead plug;
at least one distal electrode support member at the distal end of the stimulation electrode lead, said support member supporting at least one electrode and being connected by a conductor link to a distal end of a first, extended portion of the electrode lead, wherein the conductor link is preformed such that, when in a relaxed state, the conductor link is not extended and may be elastically extended;
a guide wire extending from the proximal end to the distal end of the stimulation electrode lead, wherein the conductor link does not provide a lumen for the guide wire,
a lumen of the first, extended portion of the electrode lead, wherein said lumen leads at the distal end of the first, extended portion of the electrode lead into a distal opening through which said guide wire may exit the stimulation electrode lead; and
a longitudinal opening of the distal electrode support member through which a distal end of said guide wire may enter the distal electrode support member.

2. The stimulation electrode lead of claim 1 wherein the conductor link comprises at least one electrical conductor surrounded by an elastic, preformed plastic sleeve and contacting an electrode on the distal electrode support member.

3. The stimulation electrode lead of claim 2 wherein the conductor link is preformed in a substantially snake-like shape.

4. The stimulation electrode lead of claim 2 wherein the conductor link is preformed in a substantially helical shape.

5. The stimulation electrode lead of claim 1 further comprising a proximal electrode support member disposed at a distal end of the first, extended portion of the electrode lead.

6. The stimulation electrode lead of claim 5 wherein at least the proximal electrode support member or both the proximal electrode support member and the distal electrode support member have a larger outer diameter than at least a portion of the first, extended portion of the electrode lead which adjoins the proximal electrode support member.

7. The stimulation electrode lead of claim 6 wherein the conductor link has a smaller outer diameter than at least the portion of the first, extended portion of the electrode lead that adjoins the proximal electrode support member.

8. The stimulation electrode lead of claim 7 wherein both said electrode support members have approximately the same outer diameter.

9. The stimulation electrode lead of claim 8 wherein the proximal electrode support member has the distal opening through which the guide wire may exit, and the longitudinal opening in the distal electrode support member is configured such that the guide wire may pass through the distal electrode support member.

10. The stimulation electrode lead of claim 9 wherein the distal opening in the proximal electrode support member has a greater inner diameter than the longitudinal opening in the distal electrode support member.

11. The stimulation electrode lead of claim 10 wherein at least one of the electrode support members is a plastic or a ceramic member.

12. The stimulation electrode lead of claim 11 wherein at least one of the electrode support members is of a length of between about 1 mm and 3 mm.

13. The stimulation electrode lead of claim 12 wherein a distal end portion of the first, extended portion of the electrode lead, the electrode support members, and the conductor link are configured to be suitable for placement in a coronary sinus or in a lateral vein branching off of the coronary sinus of a heart.

14. The stimulation electrode lead of claim 13 wherein the conductor link has a significantly smaller diameter than the distal electrode support member, and adjoins the proximal electrode lead portion laterally with respect to a central longitudinal axis of the stimulation electrode lead, adjacent the distal opening in the proximal electrode lead portion.

15. The stimulation electrode lead of claim 14 wherein the conductor link adjoins the distal electrode support member laterally, adjacent the longitudinal opening in the distal electrode support member.

16. The stimulation electrode lead of claim 5 wherein the conductor link has a smaller outer diameter than at least the portion of the first, extended portion of the electrode lead that adjoins the proximal electrode support member.

17. The stimulation electrode lead of claim 5 wherein both said electrode support members have approximately the same outer diameter.

18. The stimulation electrode lead of claim 5 wherein the proximal electrode support member has the distal opening through which the guide wire may exit, and the longitudinal opening in the distal electrode support member is configured such that the guide wire may pass through the distal electrode support member.

19. The stimulation electrode lead of claim 5 wherein at least one of the electrode support members is a plastic or a ceramic member.

20. The stimulation electrode lead of claim 1 wherein the conductor link is preformed in a substantially snake-like shape.

21. The stimulation electrode lead of claim 1 wherein the conductor link is preformed in a substantially helical shape.

22. The stimulation electrode lead of claim 1 further comprising a proximal electrode support member disposed at a distal end of the first, extended portion of the electrode lead.

23. The stimulation electrode lead of claim 1 wherein at least one of the electrode support members is of a length of between about 1 mm and 3 mm.

24. The stimulation electrode lead of claim 1 wherein a distal end portion of the first, extended portion of the electrode lead, the electrode support members, and the conductor link are configured to be suitable for placement in a coronary sinus or in a lateral vein branching off of the coronary sinus of a heart.

25. The stimulation electrode lead of claim 1 wherein the conductor link has a significantly smaller diameter than the distal electrode support member, and adjoins the proximal electrode lead portion laterally with respect to a central longitudinal axis of the stimulation electrode lead, adjacent the distal opening in the proximal electrode lead portion.

26. The stimulation electrode lead of claim 1 wherein the conductor link adjoins the distal electrode support member laterally, adjacent the longitudinal opening in the distal electrode support member.

* * * * *